(12) United States Patent
Kumakhov

(10) Patent No.: US 7,130,370 B2
(45) Date of Patent: *Oct. 31, 2006

(54) METHOD AND APPARATUS FOR PRODUCING AN IMAGE OF THE INTERNAL STRUCTURE OF AN OBJECT

(76) Inventor: Muradin Abubekirovich Kumakhov, ul. Narodnogo Opolcheniya, d. 38, kv. 55, Moscow 123298 (RU)

( * ) Notice: Subject to any disclaimer, the term of this patent is extended or adjusted under 35 U.S.C. 154(b) by 0 days.

This patent is subject to a terminal disclaimer.

(21) Appl. No.: 10/872,777

(22) Filed: Jun. 22, 2004

(65) Prior Publication Data

US 2005/0031078 A1 Feb. 10, 2005

Related U.S. Application Data

(63) Continuation of application No. 09/937,286, filed as application No. PCT/RU00/00207 on May 30, 2000, now Pat. No. 6,754,304.

(30) Foreign Application Priority Data

Feb. 11, 2000 (RU) ............................... 2000103190

(51) Int. Cl.
G01N 23/22 (2006.01)

(52) U.S. Cl. .............................. 378/45; 378/87; 378/88

(58) Field of Classification Search ............ 378/44–46, 378/50, 84–90, 119, 147, 149, 49, 70
See application file for complete search history.

(56) References Cited

U.S. PATENT DOCUMENTS

| | | | | |
|---|---|---|---|---|
| 3,418,467 A | * | 12/1968 | Ladell et al. ................ 378/119 |
| 3,980,568 A | * | 9/1976 | Pitchford et al. .............. 378/46 |
| 4,817,120 A | * | 3/1989 | Pelix et al. .................... 378/45 |
| 4,852,135 A | * | 7/1989 | Anisovich et al. ............. 378/49 |
| 5,325,416 A | * | 6/1994 | Saito et al. .................... 378/50 |
| 5,497,008 A | * | 3/1996 | Kumakhov .............. 250/505.1 |
| 5,570,408 A | * | 10/1996 | Gibson ........................ 378/145 |
| 5,745,547 A | * | 4/1998 | Xiao ........................... 378/145 |
| 5,778,039 A | * | 7/1998 | Hossain et al. ............... 378/45 |

(Continued)

*Primary Examiner*—Allen C. Ho
(74) *Attorney, Agent, or Firm*—McDermott Will & Emery LLP

(57) ABSTRACT

Inventions related to the intra-vision means, designed for production of visually sensed images of the internal structure of an object, in particular, of a biological object, are aimed at higher accuracy of determining the relative density indices of the object's substance in the obtained image together with avoiding complex and expensive engineering; when used for diagnostic purposes in medicine, the dosage of tissues surrounding those that are examined is decreased. X-rays from source 1 is concentrated (for example, using X-ray lens 2) in the zone that includes the current point 4, to which the measurement results are attributed and which is located within the target area 7 of the object 5. Excited in this zone secondary scattered radiation (Compton, fluorescent) is transported (for example, using X-ray lens 3) to one or more detectors 6. By moving the said zone, the target area 7 of object 5 is scanned, and based upon population of the intensity values of the secondary radiation, which are obtained with the help of one or more detectors 6 and which are determined concurrently with coordinates of the current point 6, judgment on the density of the object's substance in this point is made. Density values together with respective coordinate values obtained using sensors 11 are used in the means 12 for data processing and imaging to build up a picture of substance density distribution in the target area of the object.

16 Claims, 6 Drawing Sheets

U.S. PATENT DOCUMENTS

| | | | |
|---|---|---|---|
| 5,812,631 A * | 9/1998 | Yan et al. .................. | 378/85 |
| 5,937,026 A * | 8/1999 | Satoh ........................ | 378/44 |
| 6,052,431 A * | 4/2000 | Onoguchi et al. ........... | 378/84 |
| 6,108,398 A * | 8/2000 | Mazor et al. ............... | 378/45 |
| 6,226,347 B1 * | 5/2001 | Golenhofen ................ | 378/45 |
| 6,345,086 B1 * | 2/2002 | Ferrandino et al. ......... | 378/44 |
| 6,370,220 B1 * | 4/2002 | Stoop ........................ | 378/45 |
| 6,381,303 B1 * | 4/2002 | Vu et al. .................... | 378/46 |
| 6,453,002 B1 * | 9/2002 | Mazor et al. ............... | 378/49 |
| 6,477,227 B1 * | 11/2002 | Kaiser et al. ............... | 378/45 |
| 6,754,304 B1 * | 6/2004 | Kumakhov .................. | 378/45 |

\* cited by examiner

METHOD AND APPARATUS FOR PRODUCING AN IMAGE OF THE INTERNAL STRUCTURE OF AN OBJECT

This is a continuation of prior application Ser. No. 09/937,286, filed Sep. 25, 2001, as the national stage of International Application PCT/RU00/00207, filed May 30, 2000, now U.S. Pat. No. 6,754,304 B1.

BACKGROUND OF THE INVENTION

1. Field of the Invention

The suggested inventions relate to the intra-vision means and are designed for producing visually sensed images of the internal structure of an object, in particular, of a biological object, with X-rays. The preferential applications include defectoscopy and medical diagnostics.

2. Description of the Prior Art

Various methods and devices of the said intended use are known, where traditional principles of projection roentgenoscopy are embodied. In such methods and devices, the visible image of the object's internal structure, for example, tissues of a biological object, is obtained as a shadow projection. Density of the acquired image in each of its points is determined by the total attenuation of X-rays that passed through the object on their way from the source to the detection means. The latter is either a fluorescent screen or an X-ray film, which should be chemically treated to get the image visualized (see Polytechnical Dictionary. Moscow, "Soviet Encyclopedia", 1976 [1], p. 425; Physics of image visualization in medicine. Edited by S. Webb. Moscow, "Mir", 1991 [2], p. 40–41).

In the above mentioned known methods and devices, the image of a real three-dimensional structure is acquired as the said two-dimensional shadow projection, which interpretation requires from the specialist who carries out object analysis, in particular, technical or medical diagnostics, respective experience and qualification and, in a number of cases, is problematic. The reasons for this are low contrast, poor signal to noise ratio, inevitable overlapping of the images of structural elements, impossibility of quantitative comparison between individual local fragments by density. Sharpness and contrast of the acquired image also decrease under the influence of quanta of the secondary Compton scattered radiation, hitting the detection means.

X-ray computer tomography methods and devices permitting to acquire a two-dimensional image of a thin layer of a three-dimensional object are known (V. V. Piklov, N. G. Preobrazhenskiy. Computational tomography and physical experiment. The progress of physical sciences, v. 141, $3^{rd}$ ed., November 1983, p. 469–498 [3]; see also [2], p. 138–146). Such methods are using multiple irradiation of the object under study from different positions and registration of the radiation that passed through this object by a line of detectors. The obtained tissue density distribution of the object in the cross-section under study (target cross-section) is discrete and achieved through computer-assisted solution of combined equations, the order of which as well as the number of resolution elements correspond to the product of the number of positions, from which irradiation is done, by the number of detectors. Doing irradiation in different cross-sections, one can obtain a three-dimensional image of the object based on a set of two-dimensional by-layer images. Computer tomography means permit in principle to obtain an image of sufficiently high quality, and this image presents the picture of tissues density distribution (in contrast to a picture specific to integral absorption of a substance (for example, biological tissues), located in the path of radiation from the source to this or that element of the observed projection.) But this is achieved through a greater number of positions, from which irradiation is done. In this case, the dose of radiation absorbed by the substance is higher, which is undesirable (and in medical applications, is most frequently inadmissible). Presence of Compton scattered radiation is a nuisance factor in this group of known methods and devices too. Both groups of methods and devices used for medical applications are also characterized by the fact, that tissues and organs, which present no interest in the study but are located in the radiation path (both in front and behind the target area), also suffer from intensive radiation (to a lesser degree in the second group of methods and devices than in the first group of methods and devices because when different positions are selected, different tissues and organs surrounding those that are under study are irradiated).

Higher resolving power in the second group of means, requiring a greater number of irradiations from different positions, is limited, first of all, due to inadmissible growth of the dosage. Technical means for acquiring primary data and further image reconstruction is quite complex due to necessity of using fast computers with special software and high-precision requirements to the mechanical structural elements, which must guarantee correct localization of one and the same resolution elements in the target area during their irradiation from different positions. The latter is caused by the fact that the image reconstruction calculations must use the actual data obtained from different irradiation cycles but referring to one and the same resolution elements.

The second above mentioned group of methods and devices, where discrete data on the density of each of the resolution elements is obtained, is the closest one to what is suggested.

SUMMARY OF THE INVENTION

The technical result, which the suggested inventions are aimed at, consists in higher accuracy of determining relative indices of the object's substance density in the acquired image together with avoided use of complex and expensive technical means. When the suggested inventions are used for diagnostic purposes in medicine and other investigations related to the action on biological objects, the achieved result consists also in reduced dosage of radiation of tissues surrounding the tissues under study.

To obtain the said types of technical results, in the suggested X-ray method of producing the image of the internal structure of an object, the X-rays are concentrated in a zone, which is located inside the area under study (which area is hereinafter referred to as the target area) of the object. Secondary radiation (scattered Compton coherent and non-coherent, fluorescent radiation), excited in this zone, is transported to one or more detectors. Scanning of the target area of the object is done by way of moving the zone of concentration. The results of measurement at each current position of the zone of concentration (X-rays concentration zone) are attributed to one of the points inside this zone. Movement of the zone of concentration during scanning is followed by simultaneous determination and fixation of coordinates of this zone. Judgment on the density of the object's substance in this point is made based on the population of intensity values of the secondary radiation, which are obtained with the help of one or more detectors and which are determined simultaneously with the coordinates of the said current point. The obtained values, recognized as the density indices of the object's substance, together with respective values of coordinates, are used for building up a picture of the substance density distribution in the object's target area. Movement of the X-ray concentration zone for scanning the object's target area is done by way of relative movement of the object under study and the X-ray sources, which relative position between themselves remains stable, together with the X-ray concentration means, means for secondary radiation transportation to the detectors, and the detectors themselves.

It is to be understood that the X-rays concentration is done with the help of several, i.e., more than one, concentration means, using several of spaced apart x-ray sources, the beans of which reach the x-ray concentration zone via different routes, so those beams are not summarized in the object's parts outside of the x-ray concentration zone.

A common feature for the known from ([2], pp. 138–146, [3], pp. 471–472) and suggested methods is the action on the object under study with X-rays during relative movement of the object under study and the X-ray optical system including X-ray sources together with their control units and detectors.

One of the differences of the suggested method consists in the presence of the operation of concentrating X-rays in the zone covering the current point, in which it is required to determine a density value (a current point, to which the measurement results are attributed). Scanning, which presence is a common feature of the known and suggested methods, is done in a totally different way in case of the latter—by shifting the current position of the X-rays concentration zone into the vicinity of the next point, for which it is desirable to determine the density of the substance of the object under study. The difference consists also in the operation of transportation of the secondary radiation (scattered Compton coherent and non-coherent radiation, fluorescent radiation), excited in this zone, from the concentration zone to the detector (detectors).

In this instance, it is not the radiation of the source itself, which passed through the object under study, that renders action on the detector (detectors), but the said secondary radiation. Intensity of the latter, as is well known (see J. Jackson. Classical Electrodynamics. M., "Mir", 1965, pp. 537–538 [4]), when all other conditions are the same, is proportional to the density of the substance, in which this radiation is excited, regardless of the nature of this substance. Thanks to this, secondary scattered radiation, which is a nuisance factor in the known method, becomes an informative factor. Usage of current values of the secondary radiation intensity as an index of the substance density is another difference of the suggested method.

Differences of the suggested method from the known one are also characterized below, in the description of possible particular cases of its embodiment, providing for using various combinations of X-rays concentration means and transportation means for the secondary scattered radiation.

In one of such particular cases, X-rays concentration in the zone covering the current point, to which the measurement results are attributed, is done using one or more collimators. In this case, a respective number of space-apart X-ray sources are used. Transportation of the excited secondary radiation to one or more detectors is also done using one or more collimators, where all collimators are oriented so that the axes of their central channels would cross in the current point, to which the measurement results are attributed.

In another particular case, X-rays concentration in the zone is done using one or more X-ray hemilenses transforming divergent radiation of a respective number of X-ray sources into quasi-parallel radiation. Transportation of the excited secondary radiation to one or more detectors is done, in this case, using one or more X-ray hemilenses or lenses, focusing this radiation on the detectors. It is also possible to perform transportation of the secondary radiation to one or more detectors using one or more hermilenses forming quasi-parallel radiation. In this case, all X-ray lenses and hemilenses are oriented so that their optical axes would cross in the current point, to which the measurement results are attributed.

In still another particular case X-rays concentration in the zone is done using one or more X-ray hemilenses transforming the divergent radiation of a respective number of space-apart sources into quasi-parallel radiation, while transportation of the excited secondary radiation to one or more detectors is done using one or more collimators. In this case, the X-ray hemilenses and collimators are oriented so that the optical axes of all X-ray hemilenses and central channels of all collimators would cross in the current point, to which the measurement results are attributed.

X-rays concentration can be also done using one or more space-apart X-ray sources and a respective number of X-ray lenses focusing the divergent X-rays from each of the sources directly in the current point, to which the measurement results are attributed; while transportation of the excited secondary radiation to one or more detectors is done using X-ray lenses focusing this radiation on the detectors and having a second focus in the said point.

Another particular case differs from the previous one in that the transportation of excited secondary radiation to one or more detectors is done using collimators oriented so, that the optical axes of their central channels would cross in the output focus of the lens focusing divergent radiation from the source (in the common focus of more than one such lenses if more than one sources are used).

The suggested device for producing the image of the internal structure of an object with X-rays comprises a means for positioning the object under study, an X-ray optical system, a means for relative movement of the means for positioning the object under study and the X-ray optical system, a means for data processing and imaging. The device also comprises sensors for determining the coordinates of the current point, to which the measurement results are attributed and which is located inside the target area. These sensors are linked to the means for positioning the object under study and the X-ray optical system and connected through their outlets to the means for data processing and imaging. The X-ray optical system comprises one or more X-ray sources, means for concentration of the radiation from the said one or more X-ray sources in the zone covering the current point, to which the measurement results are attributed. In addition the X-ray optical system comprises one or more means for transportation of the excited secondary radiation and placed at their exits detectors of this radiation. The outlets of the said detectors are connected to the means for data processing and imaging.

A common feature of the known and suggested devices is the presence of the means for positioning the object under study, an X-ray optical system, a means for relative movement of the means for positioning the object under study and the X-ray optical system, coordinate sensors, and the means for data processing and imaging.

In contrast to the known device, the X-ray optical system in the suggested device comprises means for concentration of the radiation from one or more sources in the zone covering the current point, to which the measurement results are attributed. In addition, the X-ray optical system comprises one or more means for transportation of the excited secondary radiation to the detectors of this radiation. Thanks to this, it is this radiation that is input to the detectors but not the radiation from the source (sources) after it has passed through the object under study. The coordinate sensors in the suggested device fulfill another function compared with the known device—they are used for determining coordinates of the current point, to which the measurement results are attributed. The function of the means for data processing and imaging is also different—this means acts based on the input carrying direct data on the substance density and coordinates of the current point, to which these data are attributed. The design of the suggested device and its principle of operation create prerequisites for a situation, when there is no dependence on the accuracy or resolving power, since the performance characteristics for this device are practically fully determined by the parameters of the X-rays concentration means used.

Other differences featured by the suggested device, in various possible particular cases of its embodiment, are characterized below.

In one of such particular cases, the X-ray optical system of the suggested device includes more than one X-ray sources. In this instance, each of the means for X-rays concentration and each of the means for transportation of the excited secondary radiation to detectors are made as a collimator with its channels oriented towards the zone of concentration of the radiation from the X-ray sources. The optical axes of the central channels of all collimators cross in the current point, to which the measurement results are attributed.

In this particular case, the X-ray sources incorporated in the X-ray optical system can be quasi-point. The collimators have channels that are all focused on these sources and are fanning (widening) towards the means for positioning the object under study. Between the exit from each X-ray source and entrance to a respective collimator, there is a screen with an opening.

In the same particular case, the X-ray sources incorporated in the X-ray optical system can be extended X-ray sources. In this instance, the collimators have channels that are all coming together (narrowing down) towards the means for positioning the object under study.

In another particular case of embodiment of the suggested device, the X-ray sources incorporated in the X-ray optical system are quasi-point sources; each of the means for X-rays concentration is made as an X-ray hemilens transforming the divergent radiation of a respective source into quasi-parallel radiation; while each of the means for transportation of the excited secondary scattered Compton radiation to the detector is made as an X-ray hemilens focusing this radiation on the detector. In this instance, the optical axes of all X-ray hemilenses cross in the current point, to which the measurement results are attributed.

In the next particular case of embodiment of the suggested device, same as in the previous one, the X-ray sources incorporated in the X-ray optical system are quasi-point sources, and each of the means for X-rays concentration is made as an X-ray hemilens transforming the divergent radiation of a respective source into quasi-parallel radiation. But in contrast to the previous case, each of the means for transportation of the excited secondary radiation to the detector is made as an X-ray hemilens with its focus in the current point, to which the measurement results are attributed, which hemilens transforms the said radiation into quasi-parallel radiation and directs it to the detector. In this instance, the optical axes of all X-ray hemilenses cross in the current point, to which the measurement results are attributed.

In still another particular case, the X-ray sources incorporated in the X-ray optical system are also quasi-point sources; each of the means for X-rays concentration is made as an X-ray hemilens transforming the divergent radiation of a respective source into quasi-parallel radiation. But in contrast to the previous case, each of the means for transportation of the excited secondary radiation to the detector is made as an X-ray lens focusing this radiation on the detector and having a second focus in the X-rays concentration zone. The optical axes of all X-ray hemilenses and lenses cross in the current point, to which the measurement results are attributed.

In the next particular case, same as in the previous two, the X-ray sources incorporated in the X-ray optical system are quasi-point, and each of the means for X-rays concentration is made as an X-ray hemilens transforming the divergent radiation of a respective source into quasi-parallel radiation. In this instance, each of the means for transportation of the excited secondary radiation to the detector is made as a collimator with channels that are all fanning (widening) towards a respective detector. The optical axes of all X-ray hemilenses and central channels of collimators cross in the current point, to which the measurement results are attributed.

The X-ray optical system of the suggested device can be made as follows too. The X-ray sources incorporated therein are quasi-point sources; each of the means for X-rays concentration is made as an X-ray hemilens transforming the divergent radiation of a respective X-ray source into quasi-parallel radiation; while each of the means for transportation of the excited secondary Compton radiation to the detector is made as a collimator with channels that are all coming together (narrowing down) towards a respective detector. The optical axes of all X-ray hemilenses and central channels of collimators cross in the current point, to which the measurement results are attributed.

Another embodiment of the suggested device is also possible, where the X-ray sources incorporated in the X-ray optical system are quasi-point sources; each of the means for X-rays concentration is made as an X-ray lens focusing the divergent radiation of the X-ray source. In this instance, each of the means for transportation of excited secondary radiation to the detector is made as an X-ray lens focusing this radiation on a respective detector. The optical axes of all X-ray lenses cross in the current point, to which the measurement results are attributed.

Next particular case of embodiment of the suggested device is characterized by the fact that the X-ray sources incorporated in the X-ray optical system are quasi-point sources; each of the means for X-rays concentration is made as an X-ray lens focusing the divergent radiation of the source; while each of the means for transportation of the excited secondary radiation to the source is made as a collimator with its channels narrowing down (coming together) towards a respective detector. In this instance, the optical axes of all X-ray lenses and central channels of collimators cross in the current point, to which the measurement results are attributed.

One more particular case of the device embodiment is characterized by the fact that the X-ray sources incorporated in the X-ray optical system are quasi-point sources; each of the means for X-rays concentration is made as an X-ray lens focusing the divergent radiation of the X-ray source; while each of the means for transportation of the excited secondary Compton radiation to the detector is made as a collimator with channels widening (fanning) towards a respective detector. In this instance, the optical axes of all X-ray lenses and central channels of collimators cross in the current point, to which the measurement results are attributed.

DETAILED DESCRIPTION OF THE PREFFERED EMBODIMENTS OF THE INVENTION

Figure 1:
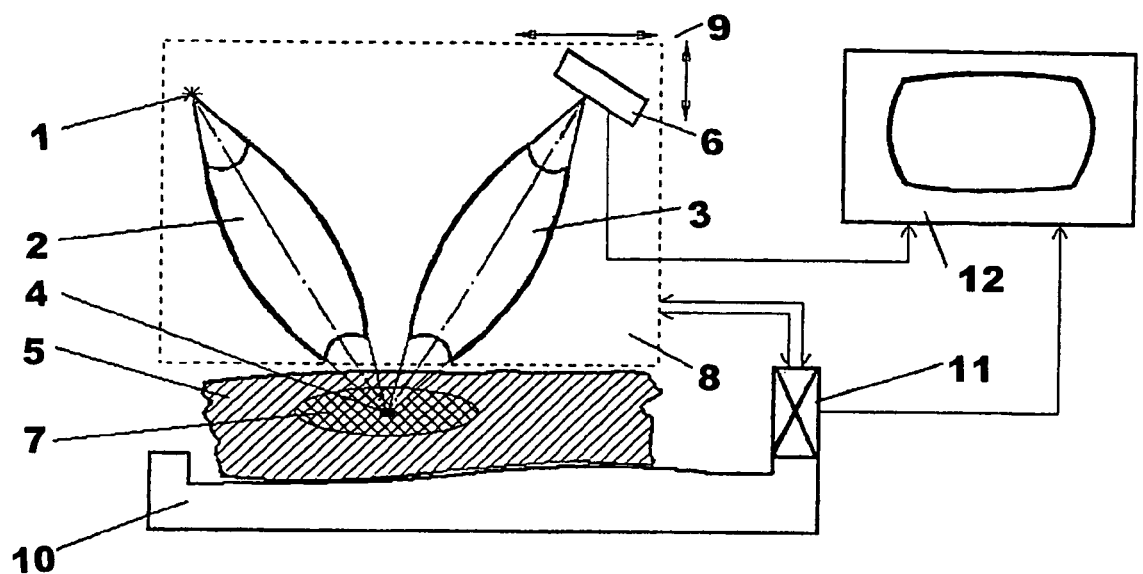
FIG. 1 clarifies the principles, on which the suggested method is based, giving a schematic diagram of positional relationships and connections between the basic components of the device embodying the suggested method.

The preferred method is embodied with the help of the suggested device as following.

Divergent X-rays from a quasi-point source (FIG. 1) is focused by the X-ray lens 2 in the specified current point 4 within the target area 7 of an object 5 (for example, a biological object). The latter is positioned as necessary with the help of the means 10 for positioning. Focused in current point 4, radiation excites secondary scattered radiation in the substance of object 5 (coherent and non-coherent Compton radiation, fluorescent radiation). The intensity of secondary radiation is proportional, with the accuracy of the fluctuations due to the stochastic nature of the process of secondary radiation excitation, to the density of the substance where it is excited. The focus of the second X-ray lens 3 is located in the same current point 4. This second lens focuses the scattered radiation that it has captured onto detector 6, which converts it into an electric signal that is input to the means 12 for data processing and imaging. The position of the common focus point of lenses 2 and 3 in point 4 is selected by way of relative movement of the means 10 for object positioning and a group of the device elements referred to as the X-ray optical system 8 comprising the X-ray source 1, the X-ray lenses 2 and 3, and the detector 6 of the secondary radiation.

It should be explained that lenses used for controlling X-rays (focusing the divergent radiation, formation of a quasi-parallel beam from divergent radiation, focusing quasi-parallel beam and so on) are a one whole of curved channels transporting the radiation, within which the radiation experiences multiple total external reflection (see, for instance: Arkadiev V. A., Kolomiytsev A. I., Kumakhov M. A. et al. Broadband X-ray optics with wide angular aperture. The Progress of Physics, 1989, vol. 157, issue 3, p. 529–537 [6], where the first lens of this type is described; U.S. Pat. No. 5,744,813 (published Apr. 28, 1998) [7], where the modern lens is described). On the whole, the lens is shaped as a barrel (i.e. it narrows down towards both ends), if it is designed for focusing the divergent radiation; or as a half-barrel (i.e. it narrows down to one of the two ends only), if it is designed for transformation of divergent radiation into quasi-parallel radiation, or for focusing such divergent radiation. The terms "full lens" and "hemilens" are widely used to determinate the lenses of two said types.

There are two options of the device operation according to FIG. 1. One option is to have the means 10 for positioning the object under study stable together with the object 5 under study located therein, while the X-ray optical system 8 is moved (the possibilities of its movement are shown by arrows 9 on FIG. 1), where the positional relationship of elements 1, 2, 3, and 6 remains fixed (consequently, coincidence of focuses of lenses 2 and 3 is preserved). The other option, on the contrary, is to have the X-ray optical system 8 fixed, while the means 10 for positioning of the object under study together with this object under study 5 is moved. Expediency of implementing one or the other option depends on the size and weight of object 5 compared to the size and weight of the group of above listed elements making the X-ray optical system 8.

The device also includes a coordinate sensor 11 that reacts to the relative movement of the X-ray optical system 8 and the means 10 for positioning of the object under study and is connected to the latter. Sensor 11 should be adjusted so as to form signals that would be proportional to the current coordinates of the common focal point of lenses 2 and 3 in point 4 relatively to the selected reference point linked to the means 10 for positioning of the object under study. Output signals from sensor 11 and the output signal from detector 6 are input to the means 12 for data processing and imaging. Focal point in point 4, in this case, is the current point, to which the measurement results are attributed and in which vicinity (with regard to the final size of the focal zone of X-ray lens 2), the radiation from the source 1 is actually concentrated. Means 12 for data processing and imaging provides for reproduction of the picture of density distribution in the object's substance through implementation of this or other two- or three-dimensional imaging algorithm (see, for instance, E. Lapshin. Graphics for IBM PC. M., "Solon", 1995 [5]). In the simplest case, when, for example, scanning (movement of the X-rays concentration zone that includes current point 4, to which the measurement results are attributed) is done in any flat cross-section of object 5, concurrently image rastering goes on the screen of means 12 with a prolonged afterglow; it is also possible to save a certain amount of measurements' results provided with a later periodic image rastering, etc.

The principle of operation of the suggested inventions is based on the fact that the intensity of secondary scattered Compton radiation (the probability of appearance of quanta of this radiation), when all other conditions are the same (in particular, in case of the same intensity of primary X-rays acting on the substance), is proportional to the substance density.

As has been noted above in the subject matter of the suggested method and device, the main difference of these inventions consists in using quanta of the scattered secondary Compton radiation as informative in contrast to known methods and devices where they are an adverse factor.

As has been noted, in medical applications an important advantage of the suggested inventions is the possibility of obtaining acceptable accuracy at lower dosage received by biological tissues.

To assess possible benefit, let's make the following assumptions: energy of photons E=50 keV, X-rays concentration zone is located at 50 mm depth and has the size of 1 mm×1 mm×1 mm (such values are typical, for example, for observation conditions and accuracy in mammography examinations); the detector registers 5% of the secondary radiation that was excited at the depth of 5 cm (this assumption means that secondary radiation, before it enters the means for its transportation to the detector, passes 5 cm in the patient's body; in this instance the angle of capture of a lens or a collimator delivering secondary radiation to the detector makes 0.05×4π steradian). Considering that photons' linear attenuation coefficient in a patient's body is close to that typical for water at E=50 keV energy and equals approximately to $2\times10^{-1}$ 1/cm, we derive, that when the primary X-ray beam reaches the depth of 5 cm, its intensity falls down in $\exp(2\times10^{-1}\times5)=e\approx2.71$ times. When the secondary radiation (which photon energy is also very close to 50 keV), leaves the patient's body, its intensity also falls down in $e\approx2.71$ times. Hence, the total intensity loss due to radiation absorption in the patient's body will make $e\times e\approx7.3$ time. Understating the assessed benefit, we will take into consideration only the Compton component of secondary radiation. At depth $\Delta x$, the probability of secondary Compton radiation formation equals to $\omega=\sigma_k\times N_e\times\Delta x$, where $\sigma^k=6.55\times10^{-25}$ cm$^2$ is the cross-section of secondary Compton scattering; $N_e=3\times10^{23}$ 1/cm$^3$ is the density of electrons in water. Thus, at $\Delta x=1$ mm$=10^{-1}$ cm probability is $\omega=6.55\times10^{-25}\times3\times10^{23}\times10^{-1}\approx2\times10^{-2}$. In other words, formation of one secondary photon at the length of $\Delta x=1$ mm requires on average 1: $(2\times10^{-2})=50$ photons of the primary radiation.

Let's put a precondition that the error of density assessment (i.e. the error with which the quantity (number) of secondary photons is determined) is of the order of 1%. With regard to the probabilistic nature of the process, the root-mean-square value of the relative error equals to $\delta=1/(N)^{1/2}$, where N is the number of registered photons. N=10000 corresponds to $\delta=0.01$.

Now we can set up a simple equation for $N_x$, i.e. the required number of primary photons penetrating to the 5 cm depth and exciting, at this depth, secondary Compton radiation, which, in its turn, passes 5 cm to reach the detector; in this instance, N=10000 photons reach the detector:

$$N_x \times e^{-2} \times 5 \times 10^{-2} \times 2 \times 10^{-2} = 10^4.$$

Here coefficient $5\times10^{-2}$ means that out of the total number of generated secondary photons, only $5\%=10^{-2}$ reach the detector and get registered. We obtain from the equation that $N_x=7.3\times10^7$.

Photons featuring energy E=50 keV produce a dose of radiation equal to 1 Roentgen, if their flux equals to $2.8\times10^{10}$ 1/cm$^2$ (for table data showing the correlation between photon energy, their number and dose see, for example, [2]). If the cross-section of the primary X-rays at their entry to the patient's body is assumed equal to 1 cm$^2$, then the flux of $7.3\times10^7$ 1/cm$^2$ will produce in the patient's body a dose of radiation equal to $2.6\times10^{-3}$ Roentgen.

During traditional X-ray tomography, for example, during osteoporosis examination, the dosage usually makes 100÷300 milliroentgen, (V. I. Mazurov, E. G. Zotkin. Topical questions of osteoporosis diagnostics and treatment. Saint-Petersburg, IKF "Toliant", 1998, p. 47 [8]), i.e. approximately 100 times higher.

Dosage can be further decreased several times if exposure is done using several sources, which beams reach the X-rays concentration zone via different routs, so those beams are not summarized in the patient's body.

Therefore, such options of embodiment of the suggested method and devices are more expedient, where several space-apart X-ray sources and X-ray detectors are used together with a respective number of the means for X-rays concentration and means for transportation of the secondary Compton radiation to the detectors (lenses, hemilenses, collimators). On one hand, it enables a more efficient X-rays concentration (in case of a sole the means for X-rays concentration, this is possible only using an X-ray lens as shown on FIG. 1) and better signal-to-noise ratio at the detector's outlet. On the other hand, this allows achieving a more distributed action of X-rays on the object under study and avoiding over dosage for the object's parts not subjected to examination. When, under all other equal conditions, several detectors and simple averaging are used (or a more complicated processing of outputs from different detectors in means 12 for data processing and imaging, as, for example, a "weighted" averaging or processing taking into account correlation of densities in the closely located points), this permits using less powerful X-ray sources without compromising the accuracy. Besides, averaging leads to less impact rendered by other factors that decrease accuracy (for example, unequal absorption of X-rays from the sources on their route to different points in which the density is determined, and that of secondary radiation on the route from such points to the entries of the means for transportation of the secondary Compton radiation to the detectors).

These are such options that are discussed below (FIGS. 2 to 11).

Figure 2:
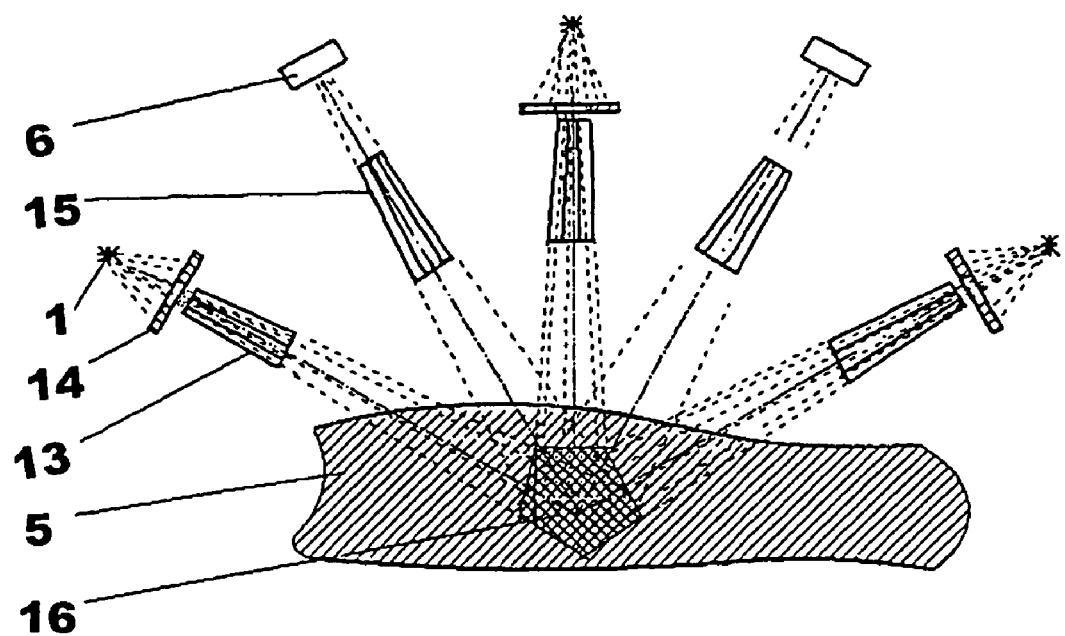
FIGS. 2 and 3 show particular cases of method embodiment and the device make, where collimators are used for X-rays concentration and transportation of the secondary radiation to detectors.
Figure 3:
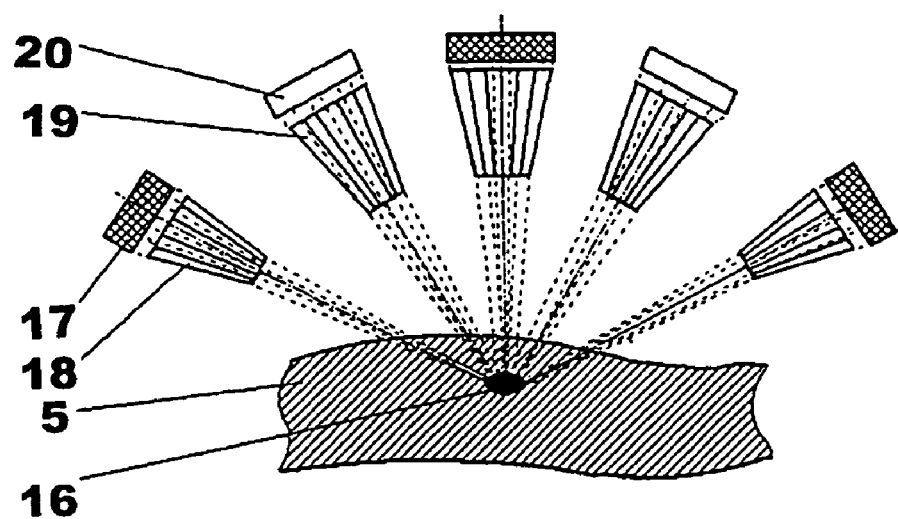

In terms of technical embodiment, the options shown in FIG. 2 and FIG. 3 are the simplest.

In the diagram on FIG. 2, quasi-point X-ray sources 1 and collimators 13 are used; the channels of collimators are fanning (widening) in the direction of radiation propagation to concentrate the radiation in zone 16. Between the sources 1 and collimators 13, there are screens 14 with openings for radiation transmission to the collimators' entries and for prevention of its direct action (aside the collimators) on the object. Secondary radiation is transported to detectors 6 with the help of collimators 15, which channels are coming together (narrowing down) in the direction of radiation propagation, i.e. towards detectors 6, and which can have a focus on the sensing surface of the latter. For instance, semiconductor detectors with small entrance aperture can be used as detectors 6.

In FIG. 3 the collimator's orientation is opposite to that shown in FIG. 2. To achieve utmost use of the entrance aperture of collimators 18, which concentrate radiation in zone 16, it is better to use extended X-ray sources 17. For the same reason, it is better to use detectors 20 featuring large entrance aperture (for example, scintillation detectors).

Figure 4:
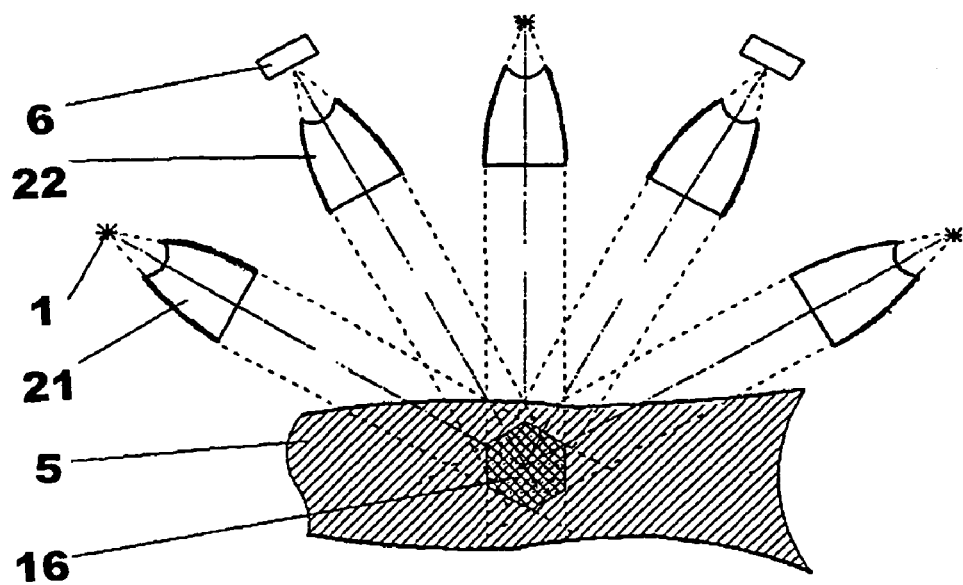
FIGS. 4 and 5 show the same with the exception that here X-ray hemilenses are used.

In FIG. 4, the X-rays concentration means for concentration of the radiation from quasi-point sources 1 and the means for transportation of the secondary radiation are made, correspondingly, as X-ray hemilenses 21 and 22. In this instance, hemilenses 22 focus secondary radiation on detectors 6.

Figure 5:
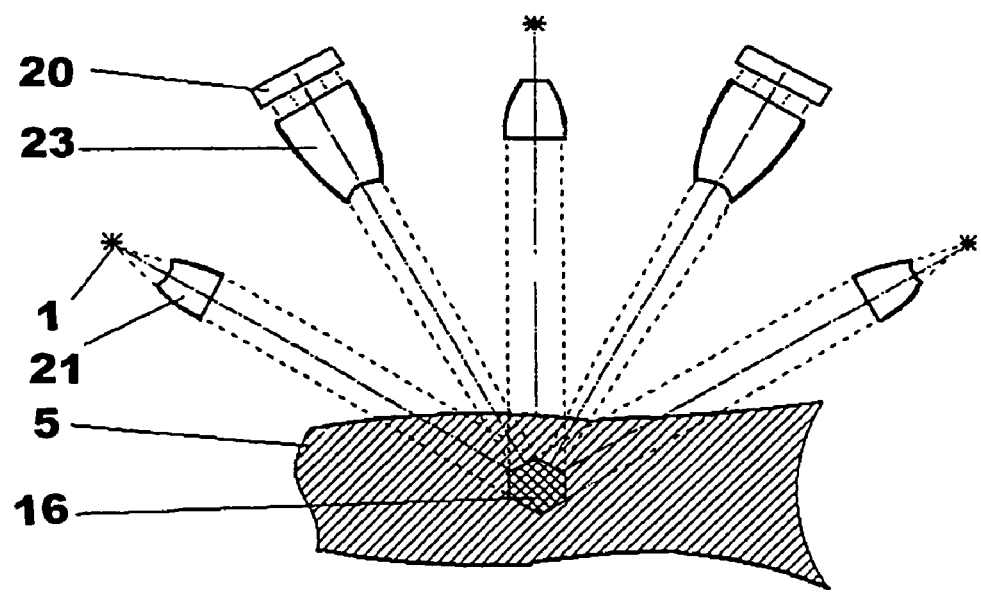

In FIG. 5, the X-rays concentration means concentrating radiation from quasi-point sources 1, and the means for transportation of the secondary radiation are made as hemilenses 21 and 23, correspondingly. In this instance, hemilenses 23 transform scattered secondary radiation into quasi-parallel radiation and direct this quasi-parallel radiation to detectors 20 featuring large entrance aperture.

Figure 6:
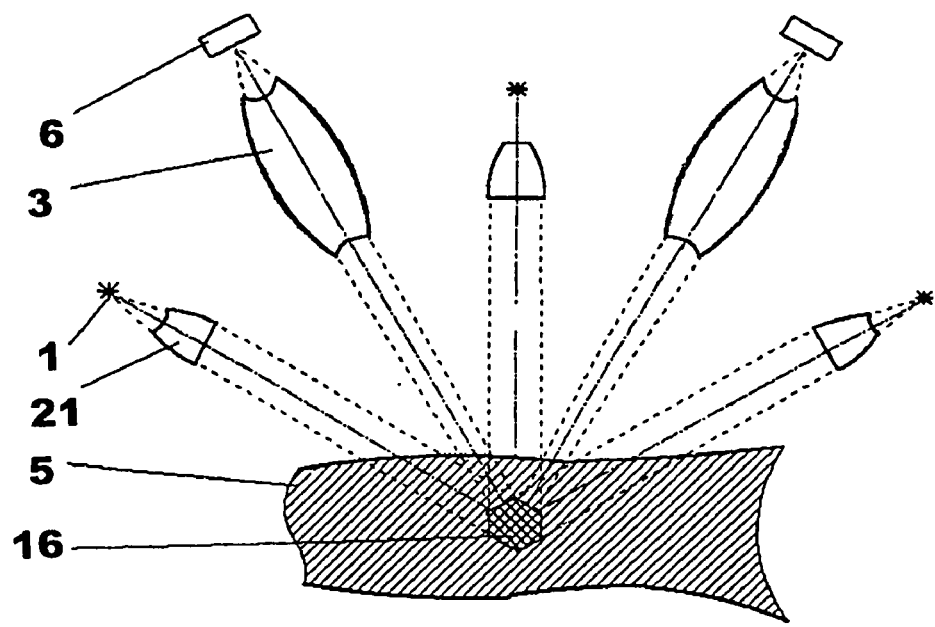
FIG. 6 shows the same with the exception that here X-ray hemilenses are used for X-rays concentration and "full" X-ray lenses are used for transportation of the secondary radiation to the detectors.

FIG. 6 shows a combined option, when the X-rays concentration means concentrating radiation from quasi-point sources 1 are made as X-ray hemilenses 21, which direct parallel beams towards zone 16; while the means for transportation of the secondary Compton radiation to detectors 6 are made as "full" X-ray lenses 3.

Figure 7:
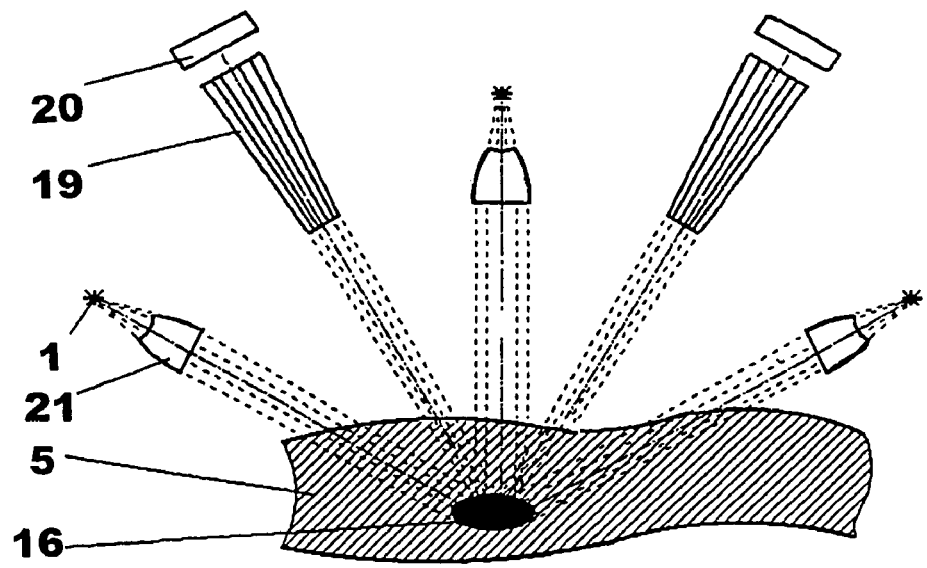
FIGS. 7 and 8 show the same with the exception that here X-ray hemilenses are used for X-rays concentration and collimators are used for transportation of the secondary radiation to detectors.
Figure 8:
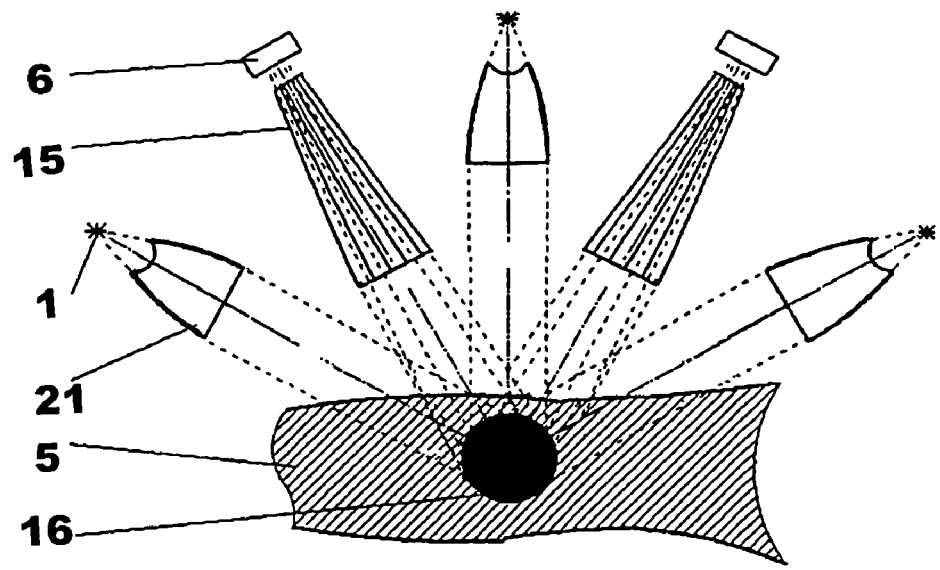

FIGS. 7 and 8 show other combinations that differ from the previous one in that the means for transportation of the secondary Compton radiation to detectors are made as collimators.

In FIG. 7, collimators 19 have channels widening towards detectors 20, while the latter have a large entrance aperture.

In FIG. 8, on the contrary, collimators 15 have channels narrowing down towards detectors 6, while the latter have a small entrance aperture.

Figure 9:
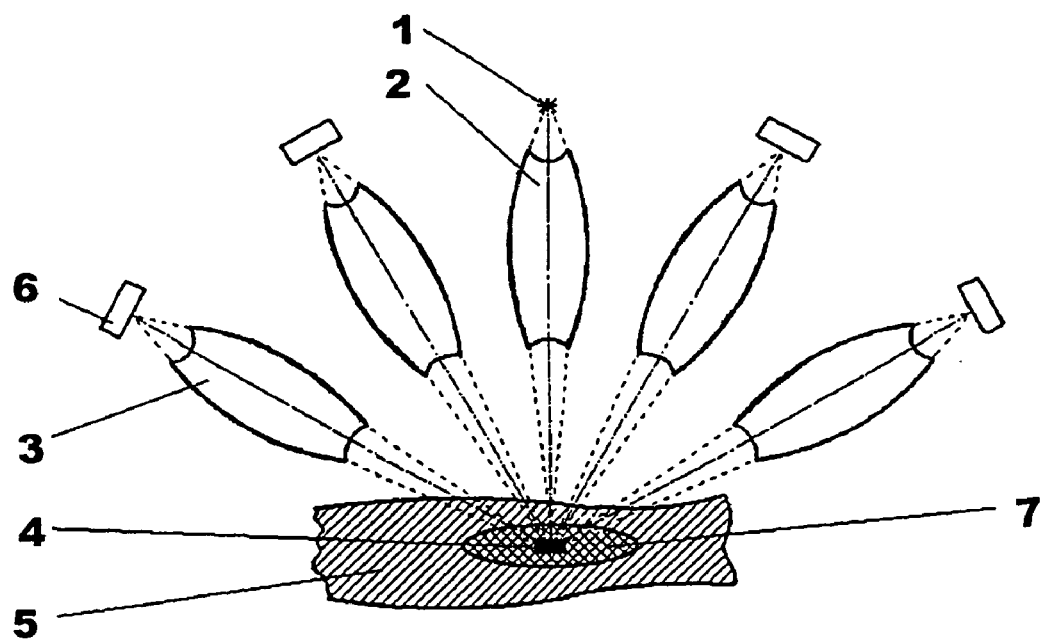
FIG. 9 shows the same with the exception that here X-ray lenses are used for X-rays concentration and transportation of the secondary radiation to the detectors.

FIG. 9 shows the most effective option in terms of accuracy and resolution, where the X-rays concentration means concentrating radiation from quasi-point sources 1 and the means for transportation of the secondary radiation to detectors 6 are made as "full" lenses 2 and 3, respectively, (compare this option with the one shown in FIG. 1).

Figure 10:
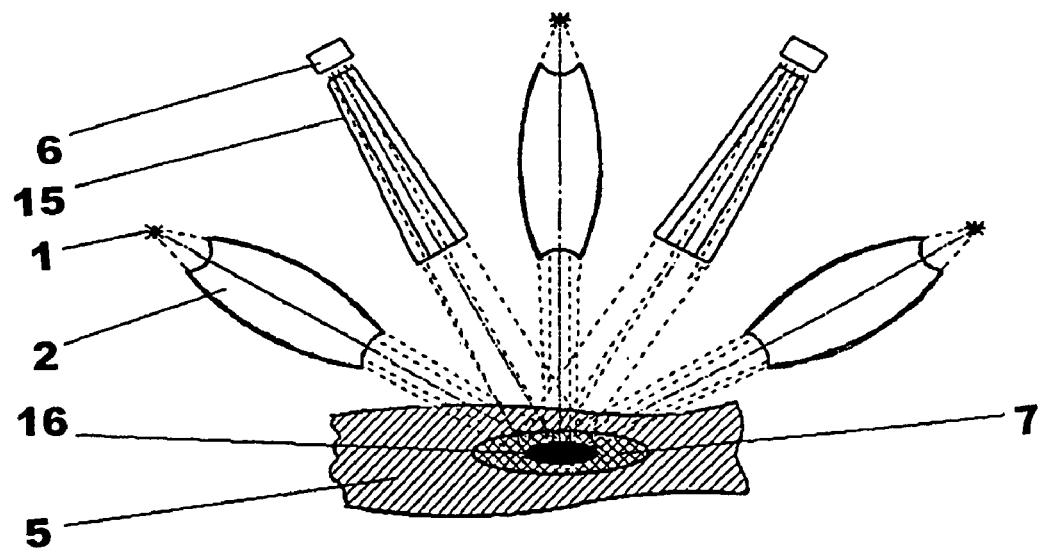
FIGS. 10 and 11 show the same with the exception that here X-ray lenses are used for X-rays concentration and collimators are used for transportation of the secondary radiation to the detectors.
Figure 11:
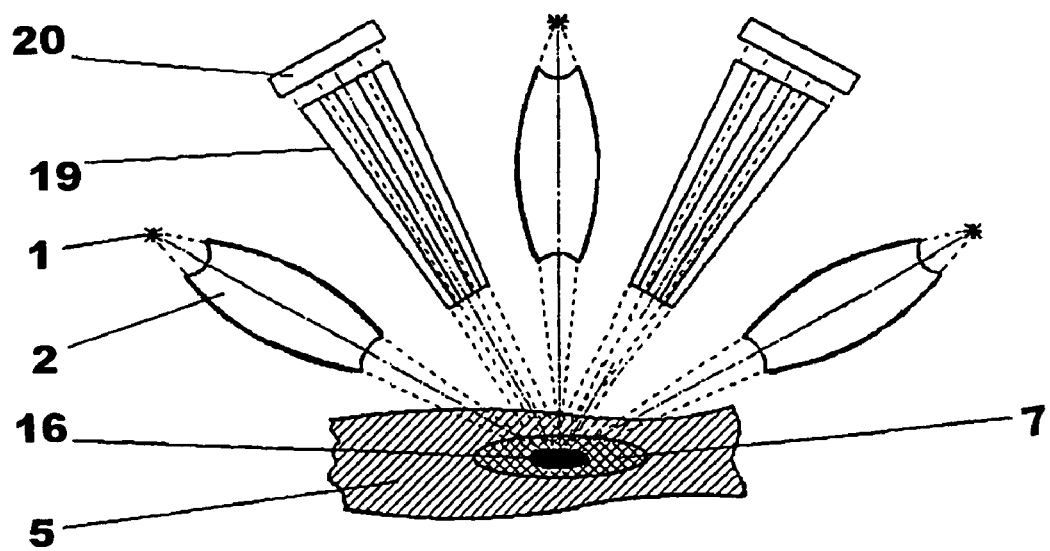

FIGS. 10 and 11 show two more combined options. Their common feature is that in both cases "full" X-ray lenses 2 are used as the X-rays concentration means concentrating radiation from quasi-point sources 1.

In FIG. 10 collimators 15 narrowing down towards the detectors are used as the means for transportation of the secondary radiation to detectors 6 featuring small aperture.

In FIG. 11 collimators 19 widening towards the detectors are used as the means for transportation of the secondary Compton radiation to detectors 20 featuring large aperture.

Utilization of one or another scheme of the method embodiment and design of the device depends both on the availability of such effective means for radiation concentration and transportation as X-ray lenses and hemilenses, and on the required resolution. The latter affects also selection of parameters for lenses and hemilenses (such as the focal spot size, length of the focus zone in the direction of the lens' optical axis, and others). This is done also taking into consideration that implementation of quite high resolution, when "full" lenses are used (of the order of some sections of a millimeter or higher), is coupled with longer time required for scanning of the object's target area. Other circumstances are also taken into account, such as availability of X-ray sources of suitable power and dimensions, and others.

Availability of the described and many other options of the suggested method embodiment and the suggested device outlays provide wide possibilities for designing intra-vision means that would satisfy specific demands.

REFERENCES

1. The Polytechnic Dictionary. M., "Soviet Encyclopedia", 1976.
2. The Physics of Image Visualization in Medicine. Ed. by S. Webb. M., "Mir", 1991.
3. V. V. Piklov, N. G. Preobrazhenskiy. Computational Tomography and Physics Experiment. The Progress of Physics, v. 141, Issue 3, November 1983.
4. J. Jackson. Classical Electrodynamics. M., "Mir", 1965
5. E. Lapshin. Graphics for IBM PC. M., "Solon", 1995
6. V. A. Arkadiev, A. I. Kolomiytsev, M. A. Kumakhov, and others. Broad-band X-ray Optics with Large Angular Aperture. The Progress of Physics, 1989, v. 157, Issue 3.
7. The U.S. Pat. No. 5,744,813 (published Apr. 28, 1998).
8. V. I. Mazurov, E. G. Zotkin. The Topical Questions of Osteoporosis Diagnostics and Treatment. Saint-Petersburg, IKF "Foliant", 1998.

The invention claimed is:

1. A method for producing an image of the internal structure of an object with X-rays, wherein said object is subjected to X-rays and the output from multiple X-ray detectors is used for obtaining data on the substance density of said object; the method including the steps of:

emitting multiple X-ray beams by multiple X-ray sources spaced apart with respect to each other, concentrating the X-ray beams in an X-ray concentration zone located within a target area of said object, the X-ray beams being concentrated using multiple concentration elements causing said X-ray beams to reach said X-ray concentration zone via multiple paths so as to sum effect of said X-rays beams in said X-ray concentration zone and avoid summing the effect of said X-ray beams in portions of said object outside of said X-ray concentration zone;

transporting secondary radiation excited in said X-ray concentration zone to the multiple detectors via multiple paths using multiple corresponding transportation elements;

determining the substance density of the object in a current point of the target area based on multiple intensity values of the secondary radiation obtained for the current point using the multiple detectors, the intensity values being determined concurrently with determining coordinates of the current point;

scanning the target area by moving said X-ray concentration zone to a next point in the target area, the scanning being performed by providing relative movement of the X-ray sources, the concentration elements, the transportation elements and the detectors with respect to the object; and producing a density distribution picture for said target area based on determined intensity values for points being scanned in the target area and determined coordinates of the respective points.

2. The method of claim 1, wherein the step of concentrating the X-ray beams includes using as the concentration elements, a plurality of collimators equal in number to said multiple spaced apart X-ray sources; said transporting of said secondary radiation from said X-ray concentration zone to said multiple detectors being performed using as the transportation elements, corresponding number of collimators having central channels, and orienting said collimators so that the axes of said central channels cross in said current point.

3. The method of claim 1, wherein the step of concentrating said X-rays includes using as the concentration elements, multiple first X-ray hemilenses for transforming divergent radiation from a respective number of said spaced apart X-ray sources into quasi-parallel radiation; said transporting of said secondary radiation excited in said X-ray concentration zone being performed using as the transportation elements, multiple second X-ray hemilenses for focusing said secondary radiation on said detectors or forming quasi-parallel radiation incident onto said detectors, and orienting said second X-ray hemilenses so that their optical axes cross in said current point.

4. The method according to claim 1, wherein the step of concentrating the X ray beams is performed using as the concentration elements, multiple X-ray hemilenses for transforming divergent radiation from a respective number of spaced apart X-ray sources in quasi-parallel radiation, transporting secondary radiation, which is excited in the X-ray concentration zone, to the multiple detectors using as the transportation elements, corresponding number of X-ray lenses for focusing this radiation on the detectors; and orienting all of said X-ray hemilenses and lenses so that their optical axes cross in the current point.

5. The method according to claim 1, wherein the step of concentrating the X-ray beams using as the concentration elements, multiple X-ray hemilenses for transforming divergent radiation from a respective number of spaced apart X-ray sources into quasi-parallel radiation;
transporting secondary radiation, which is excited in the X-ray concentration zone, to the multiple detectors using as the transportation elements, multiple collimators; orienting said X-ray hemilenses and said collimators so that the optical axes of all X-ray hemilenses and central channels of all collimators cross in the current point.

6. The method according to claim 1, wherein the step of concentrating the X-ray beams is performed using as the concentration elements, multiple X-ray lenses for focusing divergent X-rays from a respective number of spaced apart X-ray sources; transporting secondary radiation, which is excited in the X-ray concentration zone, to said multiple detectors using as the transportation elements, corresponding number of X-ray lenses focusing this radiation on said detectors.

7. The method according to claim 1, wherein the step of concentrating the X-ray beams is performed using as the concentration elements, multiple X-ray lenses for focusing divergent X-rays from respective number of spaced apart X-ray sources; and transporting secondary radiation, which is excited in the X-ray concentration zone, to said multiple detectors using as the transportation elements corresponding number of collimators.

8. Apparatus for producing an image of the internal structure of an object said apparatus including:
a holding device for holding said object;
an X-ray optical system for providing X-ray radiation and determining radiation intensity;
a moving device for providing relative movement between the holding device and the X-ray optical system to scan a target area of the object,
a coordinate sensing device for determining coordinates of points in the target area corresponding to relative positions between the holding device and the X-ray optical system, and
a processing device coupled to the X-ray optical system and the coordinate sensing device for processing information to produce the image;
the X-ray optical system including:
multiple X-ray sources spaced apart with respect to each other for producing multiple X-ray beams,
multiple X-ray concentration elements for concentrating the multiple X-ray beams in an X-ray concentration zone located within the target area of the object, the X-ray concentration elements causing the X-ray beams to reach the X-ray concentration zone via multiple paths so as to sum effect of the X-rays beams in the X-ray concentration zone and avoid summing the effect of the X-ray beams in portions of the object outside of the X-ray concentration zone,
multiple transportation elements for transporting secondary radiation excited in the X-ray concentration zone via multiple paths, and
multiple X-ray detectors corresponding to the multiple transportation elements and arranged for determining intensity of the secondary radiation for a current point in the target area; the current point corresponding to a current relative position between the holding device and the X-ray optical system,
the coordinate sensing system being configured for determining coordinates of the current point, and
the processing device being configured for receiving values of the intensity determined by the multiple X-ray detectors and for producing the image of the internal structure of the object based on the values of the intensity for various points being scanned in the target area and the coordinates of the respective points.

9. Apparatus according to claim 8, wherein said X-ray sources are quasi-point X-ray sources; each of said X-rays concentration elements being comprised of an X-ray hemilens for transforming divergent radiation from a respective X-ray source into quasi-parallel radiation; and each of said multiple X-ray transportation elements for transportation of secondary radiation to said X-ray detectors is comprised of an X-ray hemilens for focusing said secondary radiation onto a respective X-ray detector; and wherein the optical axes of all X-ray hemilenses cross in said current point.

10. Apparatus according to claim 8, wherein said X-ray sources are quasi-point X-ray sources; each of said X-rays concentration elements being comprised of an X-ray hemilens transforming divergent radiation from a respective X-ray source into quasi-parallel radiation; and each of said transportation elements for transportation of secondary radiation to said X-ray detectors is comprised of an X-ray hemilens for forming quasi-parallel radiation and having a focus in said X-rays concentration zone; wherein the optical axes of all X-ray hemilenses cross in said current point.

11. Apparatus according to claim 8, wherein said X-ray sources are quasi-point X-ray sources; each of said X-rays concentration elements being comprised of an X-ray hemilens for transforming divergent radiation from a respective X-ray source into quasi-parallel radiation; and each of said transportation elements for transportation of secondary radiation to said X-ray detector is comprised of an X-ray lens including a first focus for focusing said secondary radiation onto a respective X-ray detector and having a second focus in said X-rays concentration zone; wherein optical axes of all X-ray hemilenses and X-ray lenses cross in said current point.

12. Apparatus according to claim 8, wherein said X-ray sources are quasi-point X-ray sources; each of said X-rays concentration means being comprised of an X-ray hemilens for transforming divergent radiation from a respective X-ray source into quasi-parallel radiation; each of said transportation elements for transportation of secondary radiation to respective X-ray detector being comprised of a collimator including channels fanning towards the respective X-ray detector; and wherein optical axes of each said hemilens and central channels of each said collimator cross in said current point.

13. Apparatus according to claim 8, wherein said X-ray sources are quasi-point X-ray sources; each of said X-rays concentration elements being comprised of an X-ray hemilens for transforming divergent radiation from a respective X-ray source into quasi-parallel radiation; each of said transportation elements for transportation of secondary radiation to a respective X-ray detectors being comprised of a collimator, including channels coming together towards the respective X-ray detector; and wherein the optical axes of all X-ray hemilenses and central channels of each said collimator cross in said current point.

14. Apparatus according to claim 8, wherein said X-ray sources are quasi-point X-ray sources; each of said X-rays concentration elements being comprised of an X-ray lens for focusing divergent radiation from a respective X-ray source; each of said transportation elements for transportation of secondary radiation to an X-ray detector being comprised of an X-ray lens for focusing said secondary radiation onto a respective detector; and wherein optical axes of all X-ray lenses cross in said current point.

15. Apparatus according to claim 8, wherein said X-ray sources are quasi-point X-ray sources; each of said X-rays concentration elements being comprised of an X-ray lens for focusing divergent radiation from a respective X-ray source; each of said transportation elements for transportation of secondary radiation to said X-ray detector being comprised of a collimator including channels coming together towards a respective detector; and wherein optical axes of all X-ray lenses and central channels of each said collimator cross in said current point.

16. Apparatus according to claim 8, wherein said X-ray sources are quasi-point X-ray sources; each of said X-rays concentration elements being comprised of an X-ray lens for focusing divergent radiation from a respective X-ray source; each of said transportation elements for transportation of secondary radiation to a detector being comprised of a collimator including channels fanning towards a respective detector; wherein optical axes of all X-ray lenses and central channels of each collimator cross in said current point.

* * * * *